United States Patent [19]

Kim et al.

[11] Patent Number: 4,873,363
[45] Date of Patent: Oct. 10, 1989

[54] PROCESS FOR THE PREPARATION OF 3-(4'-BROMOBIPHENYL-4-YL)TETRALIN-1-ONE

[75] Inventors: In O. Kim; Sang G. Lee, both of Seoul, Rep. of Korea

[73] Assignee: Korea Advanced Institute of Science and Technology, Rep. of Korea

[21] Appl. No.: 192,776

[22] Filed: May 11, 1988

[30] Foreign Application Priority Data

Sep. 24, 1987 [KR] Rep. of Korea ............... 10603/1987

[51] Int. Cl.$^4$ .............................................. C07C 45/45
[52] U.S. Cl. ..................................... 568/319; 560/53; 562/492
[58] Field of Search ......................... 560/53; 562/492; 568/319

[56] References Cited

U.S. PATENT DOCUMENTS 4,035,505  7/1977  Hadler et al. ...................... 514/457

OTHER PUBLICATIONS

Fieser et al, "Reagents for Organic Synthesis", vol. 6, p. 616 (1977).

Primary Examiner—James H. Reamer
Attorney, Agent, or Firm—Darby & Darby

[57] ABSTRACT

A new process for the preparation of a 3-(4'-bromobiphenyl-4-yl)tetralin-1-one known as a key intermediate for the production of rodenticides and clinical medicines is provided. The title compound is prepared from P-bromobiphenylbenzylketone in three steps, wherein one of key inventions is dehydroxylation of 3-(4'-bromobiphenyl)-3-hydroxy-4-phenylbutyric acid ethyl ester using trialkylsilane in trifluoroacetic acid. This new process offers a high yield with a facile way and is more suitable for a commercial production than the prior art methods.

8 Claims, No Drawings

PROCESS FOR THE PREPARATION OF 3-(4′-BROMOBIPHENYL-4-YL)TETRALIN-1-ONE

BACKGROUND OF INVENTION 3-(4′-Bromobiphenyl-4-yl)tetralin-1-one of the formula IV is an useful intermediate for the production of rodenticides and clinical medicines. The compound IV is disclosed in U.S. Pat. Nos. 3,957,824 and 4,035,505 and J. Chem. Soc. Perkin I, 1190 (1976). Their two different methods for the production of a compound of the formula IV are shown in Scheme 1:

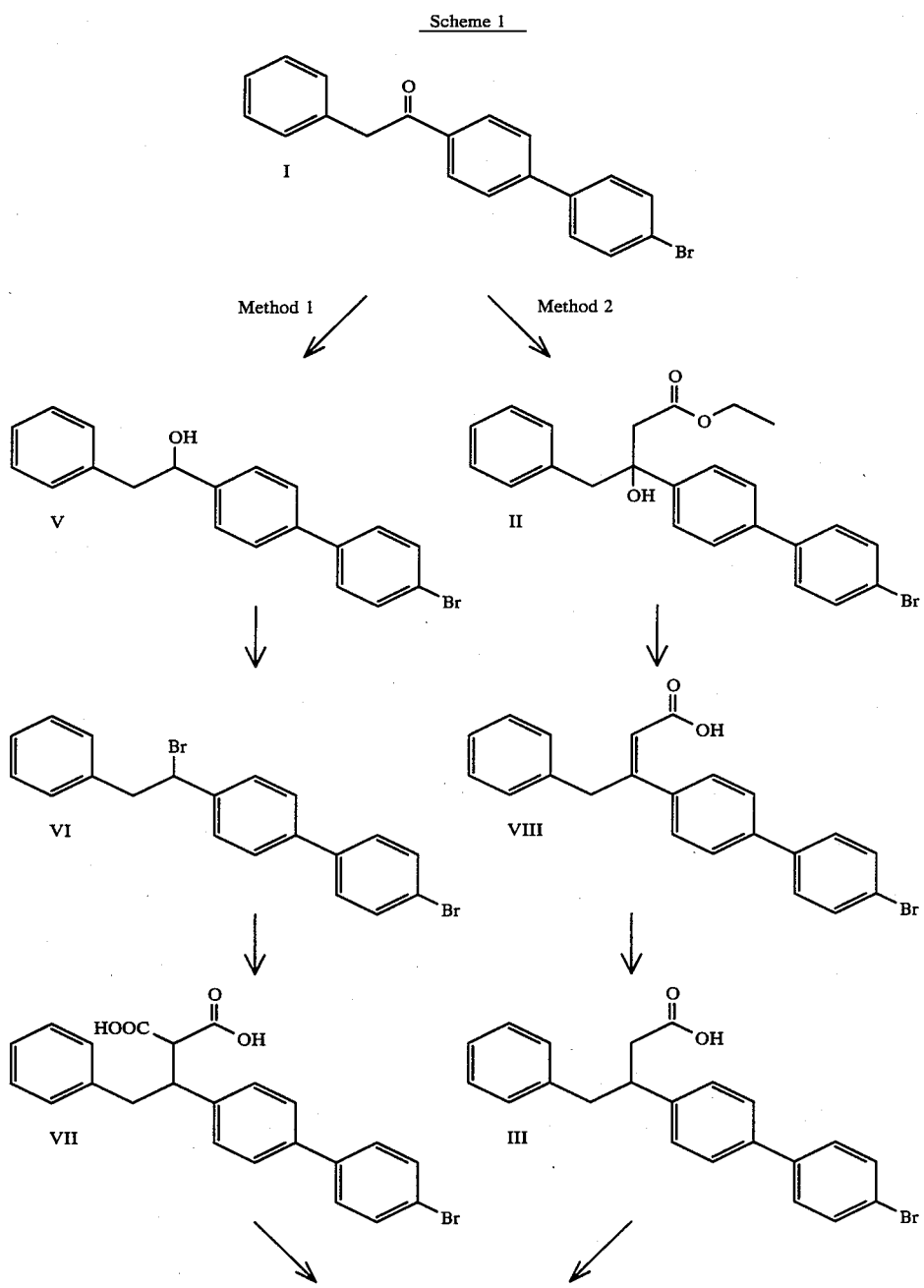

-continued

Scheme 1

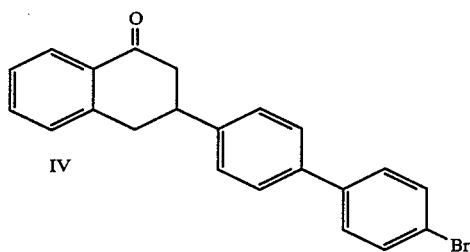

IV

The reaction of an alcohol of the formula V with phosphorus tribromide in method 1 (Scheme 1) provided a dehydrated product which had stilbene structure (4′-(4′-bromophenyl)stilbene) as a side structure as well as a desired product of the formula VI. In addition, the dehydrated product had also formed as a side product in alkylation step of bromide VI to a compound of the formula VII. Since the cyclization reaction of a compound of the formula VII underwent through decarboxylation, the high temperature was required in that step.

In method 2 (Scheme 1), the known process used the Reformatsky reaction in the first synthetic step for the production of a compound II. In that step the reaction was performed with a compound I, ethyl bromoacetate, and zinc in benzene under reflux. In their condition, the separation of the desired product from an unconsumed starting ketone I was not easy and gave low isolation yield. Dehydration reaction of a compound II was carried out with P-toluenesulfonic acid, providing a desired $\alpha,\beta$-unsaturated carboxylic acid VIII with an isomerized $\beta,\gamma$-unsaturated acid VIII which was not easily reduced to saturated carboxylic acid, as shown in Scheme 2:

Scheme 2

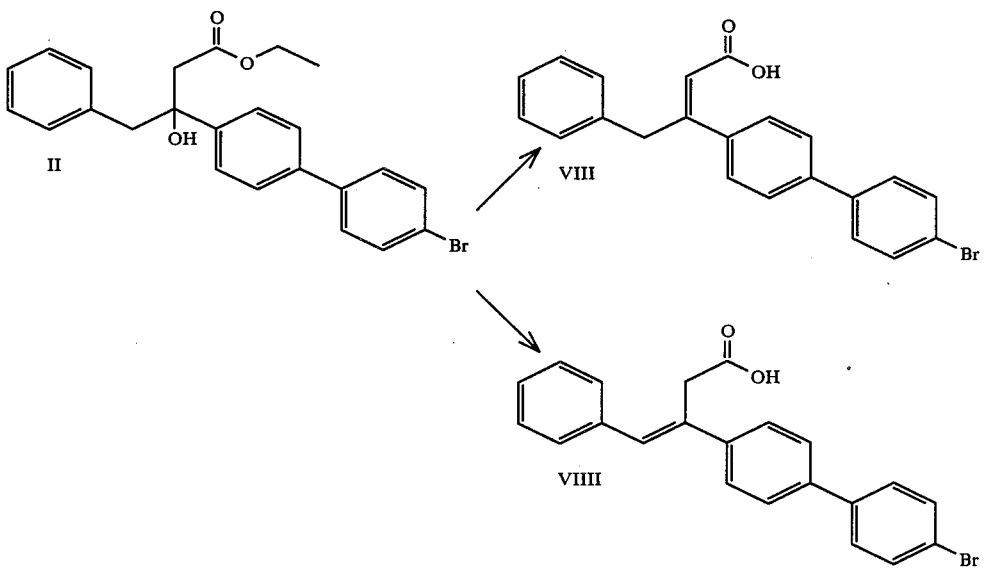

In addition, it had a difficulty to perform the cyclization reaction of a compound VIIII, because the compound VIIII in solid form was not mixed homogeneously with polyphosphoric acid.

The present invention provides a new and improved process for the preparation of 3-(4′-bromobiphenyl-4-yl)tetralin-1-one IV. And this invention overcomes the technical and economical problems shown in disclosed patents above.

DETAILED DESCRIPTION OF THE INVENTION

The present invention concern a new process for the production of 3-(4′-bromobiphenyl-4-yl)tetralin-1-one of the formula IV. The following reaction Scheme 3 is illustrative of a process for making a compound IV of this invention, and contains three steps.

Scheme 3

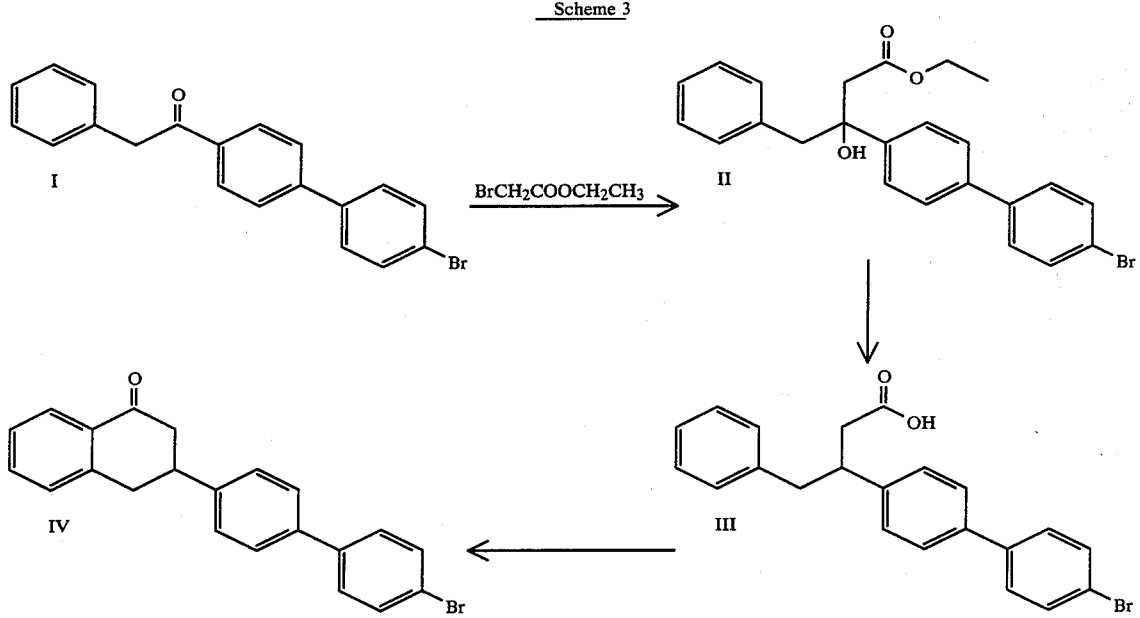

The Reformatsky reaction of ketone I with ehtyl bromoacetate provided β-hydroxycarboxylic ester II. Dehydroxylation of the compound II was carried out by the treatment of trialkylsilane in trifluoroacetic acid, and hydrolysis gave carboxylic acid III. The final desired product of the formula IV was produced by the cyclization reaction with polyphosphoric acid in a organic solvent.

In the first step, when pure benzene was used, the unreacted starting ketone I affected the reaction yield and caused a separating problem as mentioned earlier. The yield was dramatically improved by using mixed solvents wherein the mixed solvents were composed of benzene, toluene or xylene and diethyl ether, petroleum ether or ligroin in ratio of 90-60 to 10-40% (v/v). The maximum yield was obtained when 70-75% of aromatic solvent was used.

One of the imrportant invention is the conversion (the second step) from β-hydroxycarboxylate II to saturated carboxylic acid III. Instead of the dehydration-hydrolysis-hydrogenation sequence, the dehydroxylation-hydrolysis sequence provided higher yield as well as the simplicity of the performance for the preparation of the compound III. Trialkylsilane, wherein alkyl is methyl or ethyl, and trifluoroacetic acid were used in the dehydroxylation step. The high yield was obtained not only in chloroform and dichloromethane (91%), but in trifluoroacetic acid as an own solvent (90%). The range of the reaction temperature when halomethane solvent was used is from −10° C. to 60° C., but the reaction temperature should be lower than 10° C. The addition of sulfate salt such as magnesium sulfate, calcium sulfate, and sodium sulfate decreased side products. It should be noted that the catalytic amount of boron trifluoride etherate makes the reaction fast in low temperature.

In the last step, the cyclization reaction was improved by using solvent when polyphosphoric acid was mixed with a compound III in solid form. While homogeneity was not accomplished in the known procedure, the present invention gave a 93% yield by using benzene, toluene, or xylene. A compound III was dissolved in benzene, toluene, or xylene at 80°–90° C. and polyphosphoric acid was added. The solvent was removed in vacuo. After heating the reaction mixture at 135°–140° C. for 0.5–1 h, the reaction mixture was cooled to 90° C. and was extracted with toluene and hot water. The organic layer was washed with hot water serveral times. Removal of solvent in vacuo offered the title compound 3-(4′-bromobiphenyl-4-yl)tetralin-1-one IV.

As above-mentioned notes, this present invention provides an easy operable process in facile way with high yield. This new process is more suitable for a commercial production of 3-(4′-bromobiphenyl-4-yl)tetralin-1-one IV than the prior art methods.

EXAMPLE 1

3-(4′-Bromobiphenyl)-3-hydroxy-4-phenylbutyric Acid Ethyl Ester II

The mixture of zinc powder (5.24 g) and iodine (0.01 g) in Ligroin and benzene (80 mL, 25:75) was stirred under reflux for 30 min. in a four-necked flask. The resulting mixture was allowed to cool to room temperature, then P-bromobiphenylbenzylketone I (20 g) and ethyl bromoacetate II (22 mL) were added and heated at 81°–81.5° C. The reaction was initiated between 15 and 30 min; then the solution was refluxed vigorously. After 10 min, an additional 6.6 mL of ethyl bromoacetate was added dropwise for 15 min, and the resulting solution was stirred at 81°–81.5° C. for 2 h. The reaction vessel was cooled at room temperature, and 100 mL of 15% aqueous sulfuric solution added. The organic layer was washed with diluted aqueous sulfuric solution and washed with saturated brine solution until the solution was neutral, and dried (MgSO₄). The solvent was removed in vacuo and the residue was washed with 60 mL of petroleum ether, providing a white solid II (18.5 g). In addition, 5.1 g of ethyl ester II was recovered from filtrate (total 23.6 g, 94.7%); melting point; 89°–90° C.

EXAMPLE 2

3-(4'-Bromobiphenyl)-4-phenylbutyric Acid III 3-(4'-Bromobiphenyl)-3-hydroxy-4-phenylbutyric acid ethyl ester II (10 g) was dissolved in 12 mL of dichloromethane and 1.5 g of magnesium sulfate and 2.65 g of triethylsilane were added. The mixture of trifluoroacetic acid (14 mL, 20.78 g) and BF$_3$.Et$_2$O (0.3 mL) was treated dropwise. The reaction mixture was stirred at room temperature for 0.5-1 h. After the solution was filtered to separate magnesium sulfate, the solvent and trifluoroacetic acid were removed under reduced pressure. The residue was treated with ethyl alcohol (15 mL) and aqueous potassium hydroxide (3 g KOH/10 mL H$_2$O) and heated at 40° C. for 2 h. The solution was allowed to cool to 25° C. and acidified to pH 2 with a concentrated hydrochloric acid. removal of ethyl alcohol in vacuo, extraction (3 times with dichloromethane), and an additional removal of organic layer (dried, MgSO$_4$) gave a white solid of III (8.5 g, 91%); melting point; 142°-4° C.

EXAMPLE 3

3-(4'-Bromobiphenyl)-4-phenylbutyric Acid III

To cooled trifluoroacetic acid (15 mL) on an ice-water bath were added 3-(4'-bromobiphenyl)-3-hydroxy-4-phenylbutyric acid ethyl ester II (10 g), magnesium sulfate (1.5 g), and 2.65 g of triethylsilane. The mixture of trifluoroacetic acid (3.5 mL) and BF$_3$.Et$_2$O (0.3 mL) was added dropwise with keeping at 10° C. After for 0.5-1 h, the solution was filtered to separate magnesium sulfate, and trifluoroacetic acid was removed under reduced pressure. In a manner analogous to that described in Example 2, the hydrolized product 3-(4'-bromobiphenyl)-4-phenylbutyric Acid III (8.4 g, 90%) was obtained.

EXAMPLE 4

3-(4'-Bromobiphenyl-4-yl)tetralin-1-one IV 3-(4'-Bromobiphenyl)-4-phenylbutyric Acid III (10 g) was dissolved in 5 mL of toluene and the reaction mixture was heated. When the temperature of the reaction vessel reached at 90° C., the reaction mixture became clear solution, and then polyphosphoric acid (9 g) was added. Toluene was removed under vacuum, and the reaction mixture was heated at 135°-140° C. for 0.5-1 h. The solution was allowed to cool to 90° C. and 30 mL of toluene and hot water (30 mL) were added. After stirring at 90° C. for 15-20 min, the organic layer was washed with hot water. Removal of toluene in vacuo provided 3-(4'-bromobiphenyl-4-yl)tetralin-1-one IV as a white solid (8.9 g, 93%); melting point; 156°-8° C.; $^1$H NMR (CDCl$_3$) δ 2.35-3.5 (m, 5H), 7-8 (m, 12H).

What we claim is:

1. A process for the production 3-(4'-bromobiphenyl)-4-yl)tetralin-1-one of the formula IV, consisting essentially of:

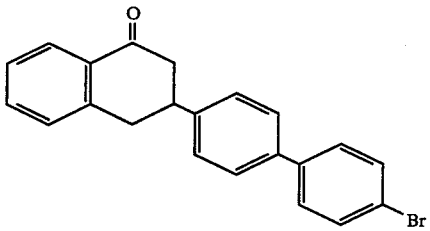

reacting a compound of formula I with ethyl bromoacetate in the presence of a mixed solvent, to form a compound of formula II;

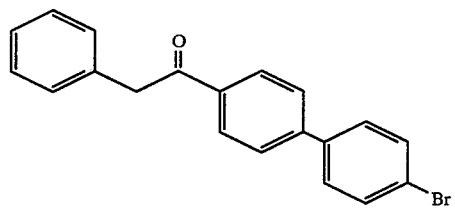

reacting the compound of formula II with trialkylsilane and trifluoroacetic acid in the presence of sulfate salt and a catalytic amount of boron trifluoride etherate wherein alkyl is 1-2 carbon atoms, to form a compound of formula III; and,

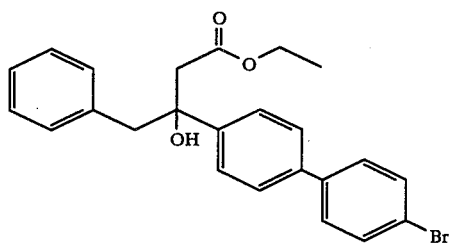

obtaining the compound of formula IV by the cyclization reaction of the compound of formula III in the presence of polyphosphoric acid in a suitable solvent:

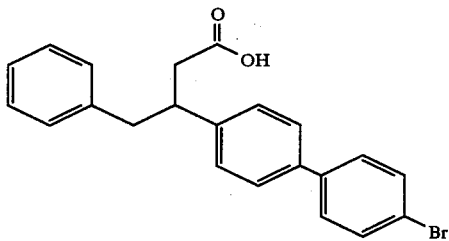

2. The process for the production of a 3-(4'-bromobiphenyl-4-yl)tetralin-1-one of the formula IV in accordance with claim 1 wherein said mixed solvents are composed of benzene, toluene or xylene and diethyl ester, petroleum ether or ligroin in ratio of 90-60 to 10-40.

3. The process for the production of a 3-(4'-bromobiphenyl-4-yl)tetralin-1-one of the formula IV in accordance with claim 1 wherein said 3-(4'-bromobiphenyl)-4-phenylbutyric acid of the formula III is obtained from the reaction of a 3-(4'-bromobiphenyl)-3- hydroxy-4-phenylbutyric acid ethyl ester of the formula II with trifluoroacetic acid and trialkylsilane in chloroform or dichloromethane.

4. The process for the production of a 3-(4'-bromobiphenyl-4-yl)tetralin-1-one of the formula IV in accordance with claim 1 wherein said trifluoroacetic acid is used as an own solvent.

5. The process for the production of a 3-(4'-bromobiphenyl-4-yl)tetralin-1-one of the formula IV in accordance with claim 1 wherein said the reaction was performed at between −10° C. and 60° C.

6. The process for the production of a 3-(4'-bromobiphenyl-4-yl)tetralin-1-one of the formula IV in accordance with claim 1 wherein said sulfate salt is magnesium sulfate, calcium sulfate, and/or sodium sulfate.

7. The process for the production of a 3-(4'-bromobiphenyl-4-yl)tetralin-1-one of the formula IV in accordance with claim 1 wherein said boron trifluoride etherate is used as a catalyst to increase the reaction rate.

8. The process of claim 1, wherein said suitable solvent is benzene, toluene or xylene.

* * * * *